United States Patent
Takimoto

(10) Patent No.: US 9,532,770 B2
(45) Date of Patent: Jan. 3, 2017

(54) ULTRASONIC DIAGNOSTIC APPARATUS AND IMAGE DATA GENERATING METHOD

(75) Inventor: Masao Takimoto, Otawara (JP)

(73) Assignee: TOSHIBA MEDICAL SYSTEMS CORPORATION, Otawara-shi (JP)

( * ) Notice: Subject to any disclaimer, the term of this patent is extended or adjusted under 35 U.S.C. 154(b) by 2575 days.

(21) Appl. No.: 11/233,065

(22) Filed: Sep. 23, 2005

(65) Prior Publication Data

US 2006/0079779 A1  Apr. 13, 2006

(30) Foreign Application Priority Data

Sep. 24, 2004  (JP) .................................. 2004-278287

(51) Int. Cl.
*A61B 8/00* (2006.01)
*A61B 8/14* (2006.01)
*G01S 7/52* (2006.01)

(52) U.S. Cl.
CPC ................. *A61B 8/546* (2013.01); *A61B 8/14* (2013.01); *G01S 7/52023* (2013.01); *G01S 7/52026* (2013.01); *G01S 7/52038* (2013.01); *G01S 7/52063* (2013.01)

(58) Field of Classification Search
CPC ....... A61B 8/546; A61B 8/14; G01S 7/52023; G01S 7/52026; G01S 7/52038; G01S 7/52063
USPC .......................... 600/459, 438, 442, 437, 449
See application file for complete search history.

(56) References Cited

U.S. PATENT DOCUMENTS

| | | | | |
|---|---|---|---|---|
| 5,158,087 A | * | 10/1992 | Gatzke | 600/459 |
| 6,436,045 B1 | * | 8/2002 | Rafter et al. | 600/447 |
| 6,663,578 B1 | * | 12/2003 | Peszynski et al. | 601/2 |
| 6,669,638 B1 | * | 12/2003 | Miller et al. | 600/438 |
| 2003/0149380 A1 | * | 8/2003 | Fujimoto et al. | 601/2 |
| 2004/0102703 A1 | * | 5/2004 | Behren et al. | 600/443 |

FOREIGN PATENT DOCUMENTS

| | | |
|---|---|---|
| JP | 9-164138 | 6/1997 |
| JP | 10-179589 | 7/1998 |
| JP | 2004-16241 | 1/2004 |

* cited by examiner

*Primary Examiner* — Long V Le
*Assistant Examiner* — Helene Bor
(74) *Attorney, Agent, or Firm* — Oblon, McClelland, Maier & Neustadt, L.L.P.

(57) ABSTRACT

An ultrasonic diagnostic apparatus comprises a driving unit, a nonlinear component extracting unit, a first image data generating unit, a second image data generating unit and a control unit. The driving unit drives an ultrasonic transducer to transmit an ultrasonic wave to a subject. The nonlinear component extracting unit extracts a nonlinear component corresponding to the ultrasonic wave from a reception signal received by the ultrasonic transducer. The first image data generating unit generates a first image data based on the nonlinear component. The second image data generating unit generates a second image data based on the reception signal. The control unit arbitrarily distributes a sound output for transmission in a definite period of time to a first ultrasonic transmission for generating the first image data and a second ultrasonic transmission for generating the second image data.

16 Claims, 6 Drawing Sheets

| | TRANSMISSION WITH LOW SOUND PRESSURE FOR B-MODE IMAGES | TRANSMISSION WITH HIGH SOUND PRESSURE FOR THI IMAGES | TRANSMISSION WITH ZERO SOUND PRESSURE |
|---|---|---|---|
| DRIVE VOLTAGE | VL | VH | 0 |
| DRIVING PERIOD | $\tau L$ | $\tau H$ | $\tau X$ |
FIG. 4
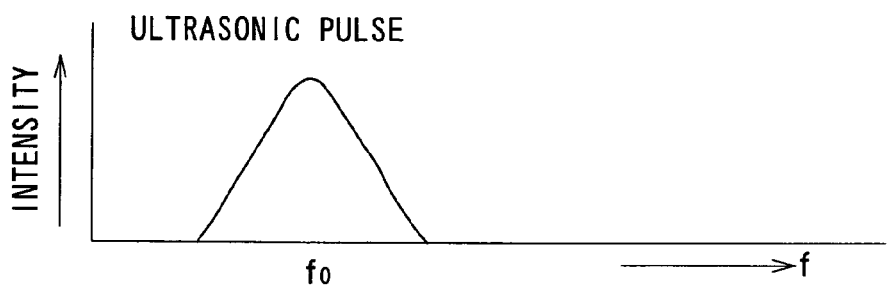
FIG. 5
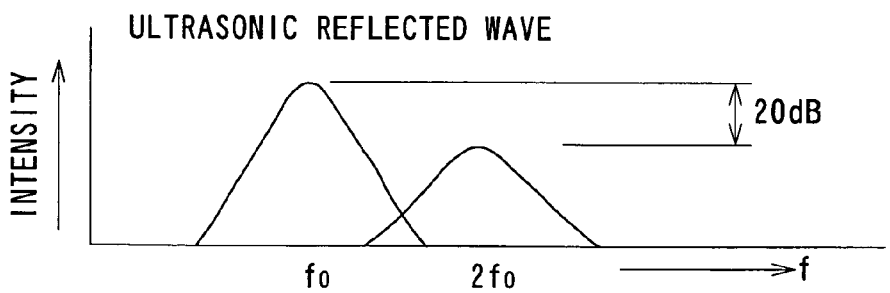
FIG. 6
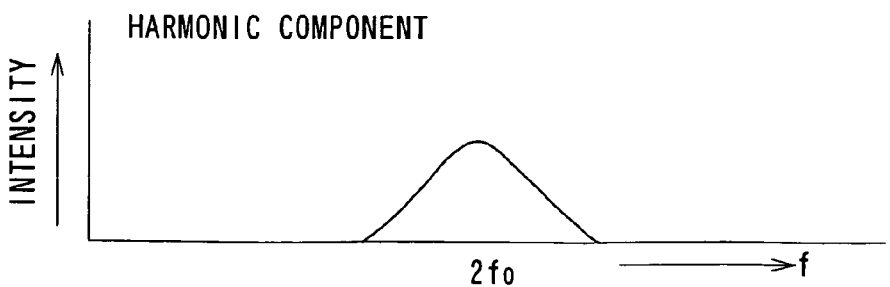
FIG. 7

ULTRASONIC DIAGNOSTIC APPARATUS AND IMAGE DATA GENERATING METHOD

BACKGROUND OF THE INVENTION

1. Field of the Invention

The present invention relates to an ultrasonic diagnostic apparatus and an image data generating method, and more particularly, to an ultrasonic diagnostic apparatus and an image data generating method which obtain ultrasonic image data with high resolution by detecting harmonic component of an ultrasonic reflected wave from a subject.

2. Description of the Related Art

An ultrasonic diagnostic apparatus serves so as to emit an ultrasonic wave generated by an ultrasonic transducer built in an ultrasonic probe into a subject, receive a reflective wave generated due to a difference in sound impedances of subject tissues by the ultrasonic transducer and display it on a monitor.

An ultrasonic diagnosis is widely used for a function test of a heart or the like, or a morphological diagnosis of a variety of organs since a two-dimensional image can be easily observed in real time by simply contacting an ultrasonic probe to the body surface. Also, since the ultrasonic diagnosis is free from radiation exposure occurring in a diagnosis with the aid of an X-ray diagnostic apparatus or an X-ray CT scanner, it has a large number of advantages, for example, not only diagnosis of a heart, an abdomen, a mammary gland, and a urinary organ but also repetitive diagnosis of a fetus in the obstetrical field, in addition to usability at bed side thanks to its small size.

In the ultrasonic diagnosis, an image data is generated by emitting an ultrasonic pulse, having its center frequency at a predetermined frequency selected depending on a diagnostic portion, into a subject and receiving an ultrasonic reflected wave having substantially the same frequency as the ultrasonic pulse.

In contrast to this, in recent years, a new imaging technology called a Tissue-Harmonic-Imaging method (hereinafter, referred to as a THI) has been developed and begins to come into wide spread use in a clinical field. With this imaging method, an ultrasonic non-linear phenomenon generated in tissue of a subject is effectively used. For example, when an ultrasonic pulse having its center frequency $f_0$ is emitted into the subject, a second harmonic component $2f_0$ newly generated due to the non-linear phenomenon of the tissues of the subject is selectively received and converted into an image.

The harmonic component is newly generated with respect to the ultrasonic pulse having a fundamental frequency (hereinafter, referred to as the fundamental component) emitted into the subject and its generation depends on the property of the subject tissue, a transmission distance to a reflective portion, and the ultrasonic intensity at the reflective portion. Hence, receiving sensitivities of a multiple reflection wave and a side lobe generated between the ultrasonic probe and an organ border and serving as the major factor of artifact in a conventional ultrasonic image can be reduced relative to that of the fundamental component. Accordingly, the THI using the harmonic component allows clear image data including little artifact to be obtained (see, for example, Japanese Patent Application (Laid-Open) No. 10-179589).

In the THI, a harmonic component is generally extracted from an ultrasonic reflected wave serving as a mixture of the fundamental and harmonic components with the filtering method. However, in the case where the fundamental and harmonic components have broadband spectra, since respective parts of the components overlap with each other, accurately extracting only the harmonic component with the filtering method is difficult.

As a method for extracting the harmonic component from such a broadband ultrasonic reflected wave, a pulse inversion method has been developed. With this method, in the case where an ultrasonic wave is transmitted/received in a predetermined direction, only the harmonic component is extracted by alternately transmitting two kinds of ultrasonic pulses having mutually different polarities so as to cancel their fundamental components by adding receiving signals obtained on this occasion to the ultrasonic pulses. The pulse inversion method is established by focusing attention on the fact that the waveform of the harmonic component is formed in proportion to the square of the amplitude of the waveform of the fundamental component and is based on the property of the ultrasonic wave that inverse of the polarity of the ultrasonic pulse causes its fundamental component to be likewise inversed but its harmonic component not to be inversed (see, for example, Japanese Patent Application (Laid-Open) No. 9-164138).

In the meantime, the harmonic component generated upon reflection of a transmission ultrasonic wave having a predetermined frequency on the tissue of the subject is significantly smaller than the fundamental component. For example, it is confirmed that the sensitivity of the second harmonic component is generally lower than that of the fundamental component by at least 20 dB although depending on the intensity of the transmission ultrasonic wave.

In addition, in the course of receiving the harmonic component reflected at the tissue of the subject by the ultrasonic probe, an ultrasonic attenuation due to absorption in the tissue depends on an ultrasonic wave frequency. For example, it is known that the ultrasonic attenuation of the foregoing second harmonic component is about two-fold in decibel unit when compared to that of the fundamental component.

With such a reason, THI image data generated on the basis of the harmonic component has a poorer S/N ratio than that of an image data generated mainly from the conventional fundamental component (i.e., an image data generated from the fundamental and harmonic components), and in particular, it is difficult to obtain a high-resolution image data of a deeply existing organ remote from the ultrasonic probe.

While two methods for improving the S/N ratio of the receiving harmonic component are provided: one for reducing noises (N) in a receiving circuit and the other for improving the receiving intensity of a signal component (S), since the former one has already reached the limit for the duty, the S/N ratio cannot be improved without the help of the latter one.

While the receiving sensitivity of the harmonic component could be improved by increasing a transmission sound output of the apparatus, when the transmission sound output is increased with a method similar to the conventional one, it is difficult to comply with the heat generation and sound output regulations of the ultrasonic probe set while taking into account the safety of the subject.

SUMMARY OF THE INVENTION

The present invention has been made in light of the conventional situations, and it is an object of the present invention to provide an ultrasonic diagnostic apparatus and an image data generating method which generate ultrasonic image data with satisfactory resolution and fewer artifacts by improving receiving sensitivity in THI without deviating from the range of exothermic regulation and sound output regulation.

The present invention provides an ultrasonic diagnostic apparatus comprising: a driving unit for driving an ultrasonic transducer to transmit an ultrasonic wave to a subject; a nonlinear component extracting unit for extracting a nonlinear component corresponding to the ultrasonic wave from a reception signal received by the ultrasonic transducer; a first image data generating unit for generating a first image data based on the nonlinear component; a second image data generating unit for generating a second image data based on the reception signal; and a control unit for arbitrarily distributing a sound output for transmission in a definite period of time to a first ultrasonic transmission for generating the first image data and a second ultrasonic transmission for generating the second image data, in an aspect to achieve the object.

The present invention also provides an image data generating method comprising steps of: driving an ultrasonic transducer to transmit an ultrasonic wave to a subject; extracting a nonlinear component corresponding to the ultrasonic wave from a reception signal received by the ultrasonic transducer; generating a first image data based on the nonlinear component; generating a second image data based on the reception signal; and arbitrarily distributing a sound output for transmission in a definite period of time to a first ultrasonic transmission for generating the first image data and a second ultrasonic transmission for generating the second image data, in an aspect to achieve the object.

The present invention as described above makes it possible to generate ultrasonic image data with satisfactory resolution and fewer artifacts since receiving sensitivity in THI is improved without deviating from the range of exothermic regulation and sound output regulation.

BRIEF DESCRIPTION OF THE DRAWINGS

In the accompanying drawings:

FIG. 4 is a diagram showing drive voltages and driving periods, stored in the sound output control unit, on transmissions with low, high and zero sound pressures according to the above-mentioned embodiment;

FIG. 5 is a figure showing an example of the frequency spectrum of the ultrasonic pulse emitted to a subject according to the above-mentioned embodiment;

FIG. 6 is a figure showing an example of the frequency spectrum of the ultrasonic reflected wave obtained with emission of the ultrasonic pulse shown in FIG. 5 according to the above-mentioned embodiment;

FIG. 7 is a figure showing an example of the frequency spectrum of the harmonic component extracted from the ultrasonic reflected wave shown in FIG. 6 in the harmonic component extracting unit according to the above-mentioned embodiment;

DESCRIPTION OF THE PREFERRED EMBODIMENTS

The present invention will now be described in further detail below with reference to an embodiment in conjunction with the accompanying drawings.

The embodiment of the present invention has a feature in inhibiting a transmission sound output and heat generation of an ultrasonic probe in a unit time within the respective regulation ranges of the sound output and the heat generation by repeating (a) a transmission of ultrasonic waves for a B-mode image with low sound pressure intended for monitoring, e.g., an operation of an apparatus and an imaging position (an image-data generating position), (b) a transmission of ultrasonic waves for a THI image with high sound pressure intended for generating diagnostic image data, and (c) a transmission with zero sound pressure intended for suspending a transmission of ultrasonic waves, all in respective predetermined periods.

While THI image data in the present embodiment is generated by applying envelope detection to the harmonic component of a receiving signal as will be described later, and is originally involved in B-mode image data, hereinafter, B-mode image data generated from the harmonic component is called THI image data and distinguished from the conventional B-mode image data generated so as to have the fundamental component as its main component.

1. Structure of the Apparatus

The whole structure of an ultrasonic diagnostic apparatus according to this embodiment will now be described in further detail below with the block diagram of FIG. 1.

Figure 1:
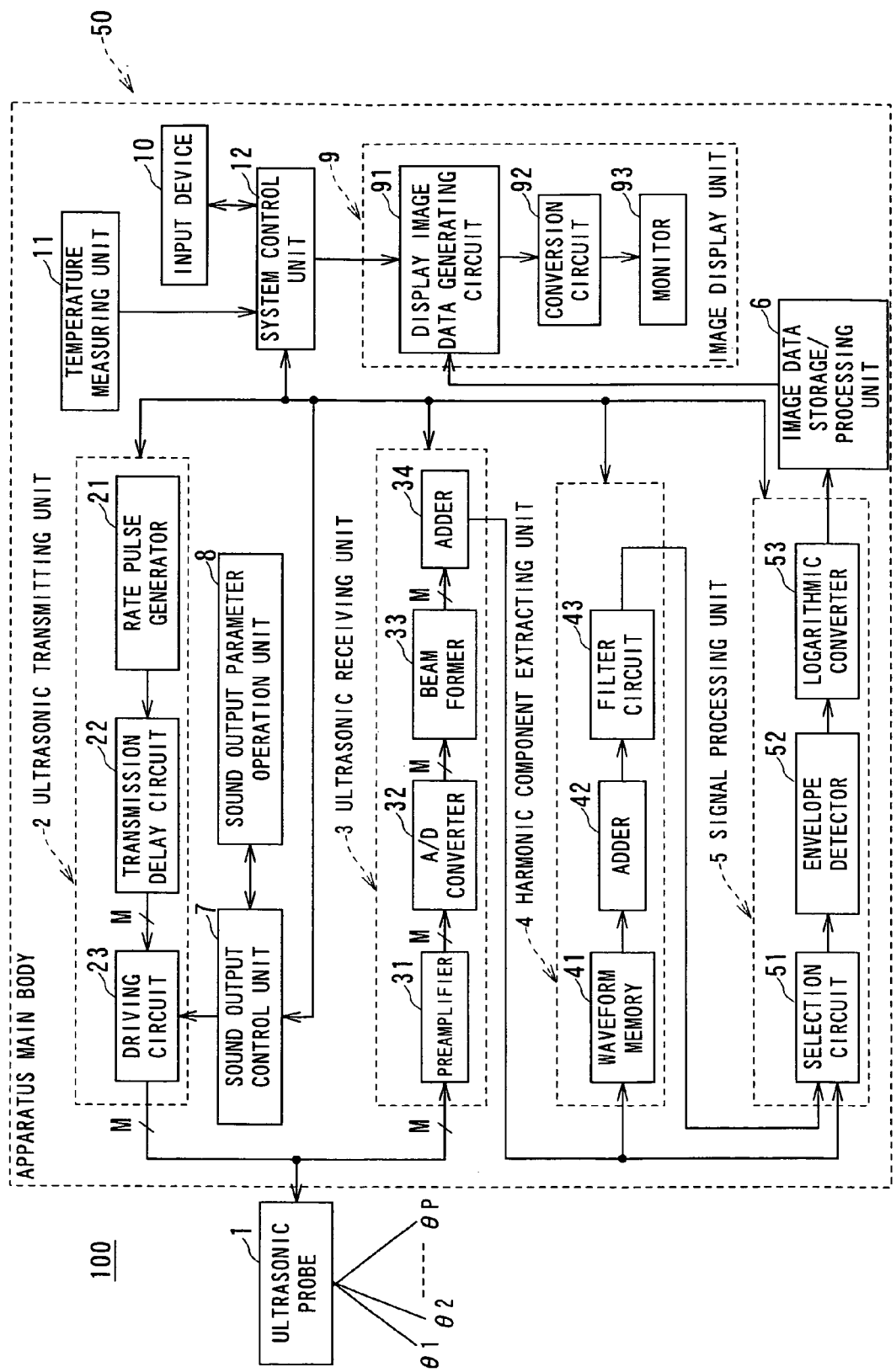
FIG. 1 is a block diagram showing a whole structure of an ultrasonic diagnostic apparatus according to an embodiment of the present invention.

An ultrasonic diagnostic apparatus 100 shown in FIG. 1 includes an ultrasonic probe 1 and an apparatus main body 50. The ultrasonic probe 1 transits an ultrasonic pulse (an ultrasonic wave for transmission) to a subject and converts an ultrasonic reflected wave (an received ultrasonic wave) to an electric signal (reception signal). The apparatus main body 50 supplies a driving signal to the ultrasonic probe 1 and generates image data in accordance with a reception signal obtained from the ultrasonic probe 1.

The ultrasonic probe 1 has a plurality of (M pieces of) ultrasonic transducers (not shown) arranged by one dimension in its end part. This end part is contacted to a subject to transmit and receive an ultrasonic wave. Each of the ultrasonic transducer in the ultrasonic probe 1 is connected to an after-mentioned ultrasonic transmitting unit 2 and an ultrasonic receiving unit 3 of the apparatus main body 50 via M channels of multi-core cables not shown.

The ultrasonic transducer is an electric-sound conversion element. This electric-sound conversion element converts an electric pulse (driving signal) to an ultrasonic pulse (an ultrasonic wave for transmission) at transmission of an ultrasonic wave and an ultrasonic reflected wave (an received ultrasonic wave) to an electrical reception signal at reception of an ultrasonic wave.

The ultrasonic probe 1 is of a sector-scanning type, a linear-scanning type, a convex-scanning type, or the like, and an operator can arbitrarily select one of them depending on a diagnostic portion. In the present embodiment, the ultrasonic probe 1 is of the sector-scanning type including M-ultrasonic transducers (i.e., the number of the transducers is M).

The apparatus main body 50 includes the ultrasonic transmitting unit 2, the ultrasonic receiving unit 3, a harmonic component extracting unit 4, a signal processing unit 5 and an image data storage/processing unit 6. The ultrasonic transmitting unit 2 generates a driving signal for emitting an ultrasonic pulse to a determined direction of a subject. The ultrasonic receiving unit 3 receives an ultrasonic reflected wave from a determined direction of a subject. The harmonic component extracting unit 4 extracts harmonic component from the reception signal received by the ultrasonic receiving unit 3. The signal processing unit 5 performs signal processing to the reception signal output from the ultrasonic receiving unit 3 and the harmonic component of the reception signal output from the harmonic component extracting unit 4 for generating B mode data and THI data. The image data storage/processing unit 6 generates B mode image data and THI image data by storing B mode data and THI data sequentially every scanning direction and performs desired image processing to these obtained image data, as needed.

The apparatus main body 50 also includes a sound output control unit 7 and a sound output parameter operation unit 8. The sound output control unit 7 performs a setup or updating of the amplitudes of driving signals, or driving periods on transmissions of ultrasonic waves, to the ultrasonic transmitting unit 2, with low sound pressure for B mode image, high sound pressure for THI image and zero sound pressure, thereby controlling a sound output of a ultrasonic wave to be transmitted from the ultrasonic probe 1 and a heat value of the ultrasonic probe 1. The sound output parameter operation unit 8 calculates the amplitudes of the driving signals, or the driving period.

The apparatus main body 50 also includes an image display unit 9, an input device 10, a temperature measuring unit 11 and a system control unit 12. The image display unit 9 displays an ultrasonic image data by performing necessary processing, such as scanning conversion or television format conversion, to the B mode image data and the THI image data generated in the image data storage/processing unit 6. The input device 10 is used for user's input operations, such as a setup of condition on an ultrasonic transmission or an input of a command signal. The temperature measuring unit 11 measures the temperature of the ultrasonic probe 1. The system control unit 12 controls overall the above-mentioned units respectively.

The ultrasonic transmitting unit 2 of the apparatus main body 50 has a rate pulse generator 21, transmission delay circuits 22 and driving circuits 23.

The rate pulse generator 21 generates rate pulses determining the repeating periods (the rate periods) of an ultrasonic pulse to be emitted into the subject and feeds to them to the transmission delay circuits 22. The transmission delay circuits 22 includes M-channel independent delay circuits, the number of which is the same as that of the ultrasonic transducers used for transmission, provide the rate pulses with focusing delay times for focusing the ultrasonic pulses at a predetermined depth and deflecting delay times for transmitting the ultrasonic pulses in a predetermined direction and feeds the rate pulses to the driving circuits 23.

The driving circuits 23 include M-channel independent driving circuits, the number of which is the same as that of the transmission delay circuits 22, drive the corresponding ultrasonic transducers built in the ultrasonic probe 1 to emit ultrasonic waves into the subject. Each of the M-channel driving circuits 23 has a pair of positive and negative polar driving circuits (not shown), respectively, generating positive and negative polar driving signals for implementing the pulse inversion method. The negative polar driving signal has a waveform characteristic formed by inversing that of the positive driving signal.

The ultrasonic receiving unit 3 of the apparatus main body 50 has a preamplifier 31 having M channels, an A/D converter 32, a beam former 33 and an adder 34.

The preamplifier 31 is designed so as to achieve a sufficient S/N ratio by amplifying a minute signal converted as an electrical receiving signal by each of the ultrasonic transducers. Each of M-channel receiving signals amplified by the preamplifier 31 so as to have a predetermined magnitude is converted into a digital signal by the A/D converter 32 and transmitted to the beam former 33.

The beam former 33 provides the corresponding one of the M-channel receiving signals outputted from the A/D converter 32 with a focusing delay time for focusing ultrasonic reflected waves from a predetermined depth and a deflecting delay time for setting receiving directivity in a predetermined direction. Then the adder 34 carries out rectifying phases and adding of these receiving signals outputted from the beam former 33. More specifically, the adder 34 carries out addition of the receiving signals obtained in a predetermined direction after rectifying their phases.

The harmonic component extracting unit 4 has a waveform memory 41, an adder 42 and a filter circuit 43. Two receiving signals in the predetermined direction, obtained by the positive and negative polar driving signals with the pulse inversion method, are temporally stored in the waveform memory 41. Then, the fundamental components of the receiving signals are canceled each other with addition of the adder 42 so as to extract the harmonic components of the same.

The filter circuit 43 includes a filter reducing the fundamental component which is not removed by the pulse inversion method due to a motion of an organ, a body motion, or the like. This filter is generally a band-pass filter (BPF) or a high pass filter (HPF).

The signal processing unit 5 has a selection circuit 51, an envelope detector 52 and a logarithmic converter 53. This signal processing unit 5 performs signal processing for generating B mode data and THI data. The selection circuit 51 selects from the harmonic component of the reception signal supplied from the filter circuit 43 of the harmonic component extracting unit 4 and the reception signal supplied directly from the adder 34 of the ultrasonic receiving unit 3.

More specifically, the selection circuit 51 selects the receiving signal fed from the adder 34 upon generating B-mode image data, and, upon generating THI image data, the harmonic component of the receiving signal fed from the filter circuit 43 of the harmonic component extracting unit 4. The envelope detector 52 applies envelope detection to the receiving signal selected by the selection circuit 51 or the harmonic component of the same and detects the corresponding envelope. The logarithmic converter 53 includes a lookup table for logarithmically converting an inputted value and outputting it so as to relatively emphasize a weak signal component by logarithmically converting the amplitude of the receiving signal.

In general, a receiving signal from the subject has amplitude having a wide dynamic range of at least 80 dB. In order to display it on a typical TV monitor having a dynamic range of about 30 dB, amplitude compression for emphasizing a weak signal component is needed.

The image data storage/processing unit 6 includes an arithmetic circuit and a memory circuit (not shown). B-mode data and THI data in a plurality of ultrasonic wave transmission/reception directions, generated by the signal processing unit 5, are sequentially stored in the memory circuit for generating B-mode image data and THI image data, respectively. The arithmetic circuit applies an image process such as edge enhancement to these pieces of image data if needed, and the processed image data is again stored in the memory circuit.

The sound output control unit 7 includes a central processing unit (CPU), a memory circuit, a lapsed time measuring circuit, and a drive voltage setting circuit (not shown). For the driving circuits 23 of the ultrasonic transmitting unit 2, the CPU sets a drive voltage $V_L$ and a driving period $\tau_L$ upon generating B-mode image data and a drive voltage $V_H$ and a driving period $\tau_H$ upon generating THI image data, in addition to setting a non-driving period (hereinafter, referred to as a transmission period with zero sound pressure) $\tau_X$.

Of five sound output parameters of the foregoing drive voltages $V_L$ and $V_H$, and driving periods $\tau_L$, $\tau_H$, and $\tau_X$, four sound output parameters are inputted from the input device 10 by the operator, and a value of the remaining sound output parameter is calculated by the sound output parameter operation unit 8, which will be described later, on the basis of the values of the inputted four sound output parameters.

The drive voltage setting circuit and the lapsed time measuring circuit of the sound output control unit 7 control the drive voltage and the driving period of the driving circuits 23, respectively, on the basis of the foregoing drive voltages $V_L$ and $V_H$ and driving periods $\tau_L$, $\tau_H$, and $\tau_X$ stored in the memory circuit.

The CPU of the sound output control unit 7 updates the driving period $\tau_H$ of the transmission for a THI image with high sound pressure to a value $\tau_{Ha}$ ($\tau_{Ha} < \tau_H$) on the basis of temperature information of the ultrasonic probe 1 fed from the temperature measuring unit 11 during generation of THI image data.

Figure 2:
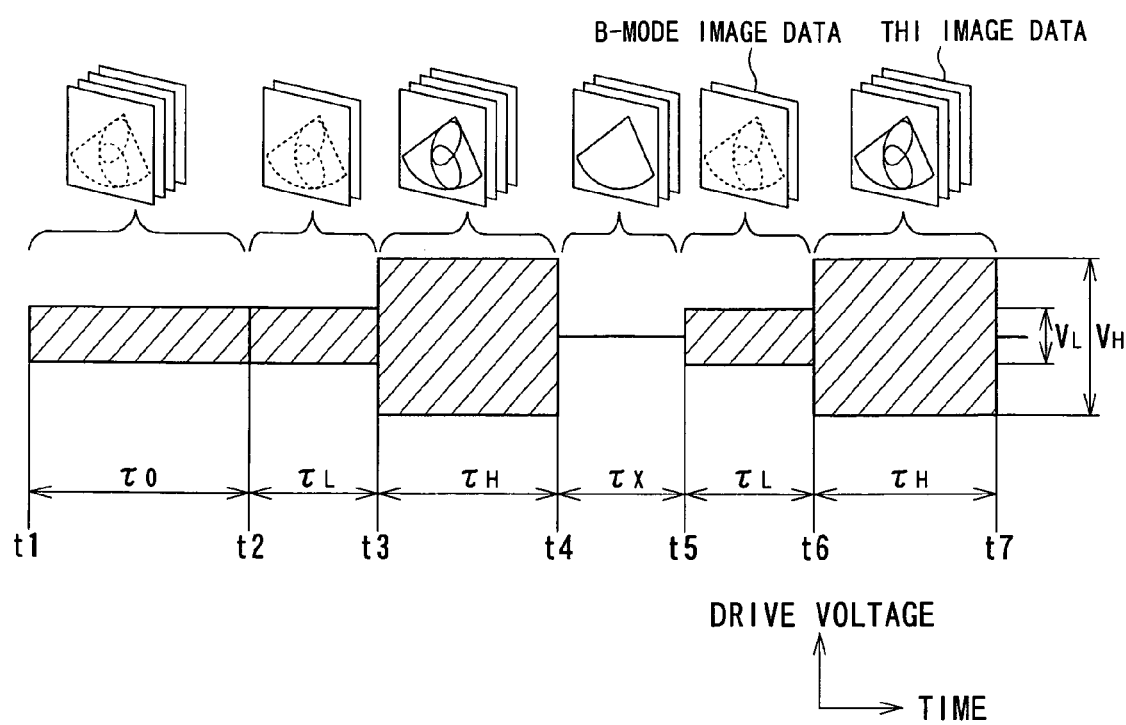
FIG. 2 is a model diagram indicating drive voltages and driving periods on transmissions with low, high and zero sound pressures according to the above-mentioned embodiment.

FIG. 2 is a diagrammatic view illustrating drive voltages and driving periods of the transmission for B-mode images with low sound pressure and the transmission for THI images with high sound pressure, and a period of the transmission with zero sound pressure set for the driving circuits 23. First, the transmission for B-mode images with low sound pressure for setting an imaging position is performed during a period $\tau_O$ from times t1 to t2, and then, the transmission for B-mode images with low sound pressure on the drive voltage $V_L$ and the transmission for THI images with high sound pressure on the drive voltage $V_H$ are performed, respectively, during the period $\tau_L$ from times t2 to t3 and the period $\tau_H$ from times t3 to t4.

Subsequently, supply of drive signals is suspended (i.e., the transmission with zero sound pressure is performed) during the period $\tau_X$ from times t4 to t5, and then, the transmission for B-mode images with low sound pressure on the drive voltage $V_L$ and the transmission for THI images with high sound pressure on the drive voltage $V_H$ are performed during the period $\tau_L$ from times t5 to t6 and the period $\tau_H$ from times t6 to t7, respectively. Likewise, the transmission with zero sound pressure, the transmission for B-mode images with low sound pressure, and the transmission for THI images with high sound pressure are repeated.

When a drive voltage according to the known B mode method is defined by $V_m$, the relationship of the foregoing drive voltages $V_L$ and $V_H$ with $V_m$ is given by $V_H > V_m > V_L$.

The sound output parameter operation unit 8 includes an arithmetic circuit and a memory circuit (not shown) and, on the basis of the four sound output parameters inputted from the input device 10, calculates the remaining sound output parameter. On this occasion, the arithmetic circuit runs a sound output parameter calculating program previously prepared on the basis of expression (1), which will be described later, and stored in the memory circuit, inputs the values of the received four sound output parameters into the program, and calculates the value of the remaining sound output parameter.

The value of the remaining sound output parameter is calculated by the sound output parameter operation unit 8 such that a sound output per unit time, on a series of the transmission for B-mode images with low sound pressure, the transmission for THI images with high sound pressure, and the transmission with zero sound pressure shown in FIG. 2 lies within the permissible range of the sound output regulation.

In this case, while it is preferable that the operator input each value of the drive voltages $V_L$ and $V_H$, and the driving periods $\tau_L$ and $\tau_H$ with the aid of the input device 10, and the sound output parameter operation unit 8 calculate the driving period $\tau_X$ of the transmission with zero sound pressure on the basis of the inputted values and the following expression (1), the present invention is not limited to the this arrangement.

$$W = \frac{K\{(V_L^2 \cdot \tau_L) + (V_H^2 \cdot \tau_H)\}}{\tau_L + \tau_H + \tau_X} \leq W_0 \approx KV_m^2 \tag{1}$$

wherein W and $W_0$ respectively stand for a transmission sound output in the present embodiment and a transmission sound output permitted by the sound output regulation both per unit time, and K stands for a proportionality constant.

The permissible transmission sound output $W_0$ is substantially equal to a transmission sound output $KV_m^2$ per unit time in accordance with the known B-mode method.

Returning to FIG. 1 again, the image display unit 9 of the apparatus main body 50 has a display image data generating circuit 91, a conversion circuit 92 and a monitor 93. The display image data generating circuit 91 generates display image data by performing processing corresponding to desired display form, such as scanning conversion, to the B mode image data and the THI image data generated in the image data storage/processing unit 6. This display image data is given to the conversion circuit 92. The conversion circuit 92 performs D/A conversion and television format conversion to the display image data to display on the monitor 93.

The input device 10 has input devices, such as a liquid-crystal-display panel, a keyboard, a trackball, and a mouse, on its operation panel. Using the input device 10, users can perform not only an input of patient information, selection of an image display mode and an input of a parameter for sound output but also an input of information, such as start command for generating B mode image data and THI image data.

The temperature measuring unit 11 has a thermistor and an A/D converter each not shown. The thermistor is arranged in or on the end part of the ultrasonic probe 1. The thermistor measures the temperature of the ultrasonic probe 1. The measured temperature serving as temperature information is given to the A/D converter. The A/D converter converts the temperature information to a digital signal and supplies the digital signal to the sound output control unit 7 through the system control unit 12.

The system control unit 12 has a CPU and a storage circuit each not shown. The system control unit 12 controls each unit to update a direction of transmission/reception of an ultrasonic wave sequentially so as to obtain image data on a determined section. The system control unit 12 also controls the whole system as well as each unit of the ultrasonic transmitting unit 2, the ultrasonic receiving unit 3, the harmonic component extracting unit 4, the image data storage/processing unit 6, the sound output control unit 7, the sound output parameter operation unit 8 and the image display unit 9 overall in accordance with an instruction signal from the input device 10.

2. Procedure of Generating Image Data

Figure 3:
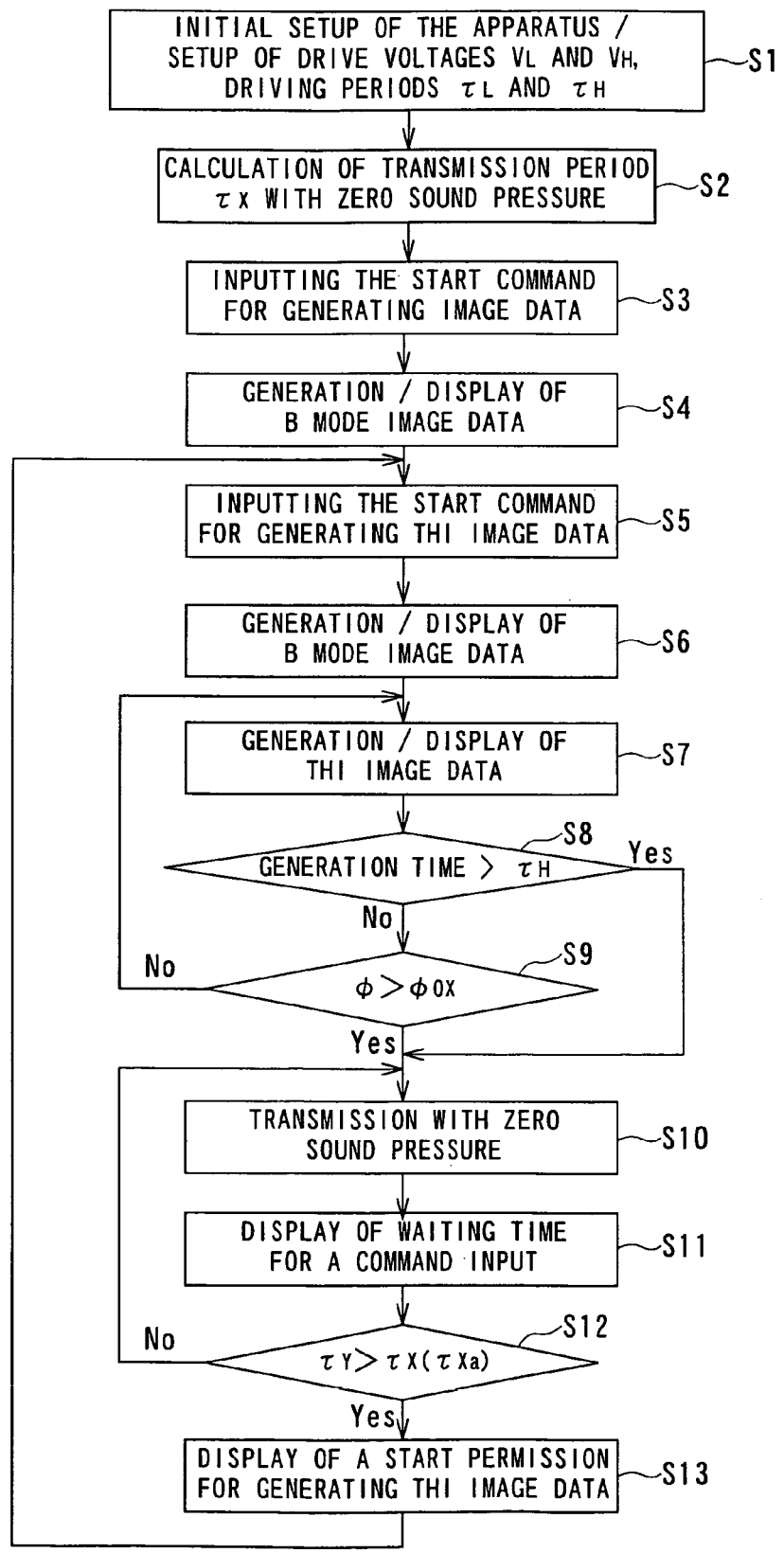
FIG. 3 is a flowchart showing a procedure for generating image data according to the above-mentioned embodiment.

Referring now to FIGS. 1 through 11, a procedure of generating B-mode image data and THI image data according to the present embodiment will be described. FIG. 3 is a flowchart indicating a procedure of generating the above-mentioned image data.

Prior to generation of image data, the operator of the ultrasonic diagnostic apparatus 100 inputs subject information with the aid of the input device 10 and selects display modes of the B-mode image data and the THI image data according to the sector scanning method, in addition to selecting application of the pulse inversion method serving as the harmonic component extracting method for generating the THI image data. Then, the operator sets the drive voltage $V_L$ and the driving period $\tau_L$ of the transmission with low sound pressure for generating the B-mode image data and the drive voltage $V_H$ and the driving period $\tau_H$ of the transmission with high sound pressure for generating the THI image data (step S1 shown in FIG. 3).

The foregoing input information, selection information, and setting conditions are stored in the memory circuit of the system control unit 12, and the drive voltages and driving periods of the respective transmissions with low and high sound pressure are stored in the memory circuit of the sound output control unit 7. The memory circuit of the sound output control unit 7 has a permissible temperature $\phi_0$ previously stored therein, regulated by the heat generation regulation.

The memory circuit of the sound output parameter operation unit 8 has the permissible transmission sound output $W_0$ per unit time previously stored therein, regulated by the sound output regulation. The sound output parameter operation unit 8 reads out the drive voltages $V_L$ and $V_H$ and the driving period $\tau_L$ and $\tau_H$ of the respective transmissions with low and high sound pressure stored in the memory circuit of the sound output control unit 7, calculates the period $\tau_X$ of the transmission with zero sound pressure by inputting the foregoing values of the sound output parameters and the permissible transmission sound output $W_0$ into the sound output parameter calculating program previously stored in the memory circuit, and stores the calculated period $\tau_X$ in the memory circuit of the sound output control unit 7 (step S2 in FIG. 3). On this occasion, the drive voltages and driving periods of the respective transmissions with low and high sound pressure and the period of the transmission with zero sound pressure are stored in the foregoing memory circuit as shown in FIG. 4.

Upon complete of the foregoing initial setting, the operator inputs a generation-starting command of the image data with the aid of the input device 10. When the generation-starting command is received by the system control unit 12, generation and display of the B-mode image data for optimizing the collection position of the image data are performed (step S3 shown in FIG. 3).

Upon generation of the B-mode image data obtained by conducting the transmission with low sound pressure, the rate pulse generator 21 feeds rate pulses to the transmission delay circuits 22, determining a repeating period (a rate period) of ultrasonic pulses to be emitted into the subject in accordance with control signals from the system control unit 12. The transmission delay circuits 22 provide the rate pulses with delay times for focusing ultrasonic waves at a predetermined depth so as to achieve a minute beam width during transmission and other delay times for emitting the ultrasonic wave in the initial scanning direction θ1 and feed this rate pulses to the driving circuits 23.

Subsequently, the driving circuits 23 drive the ultrasonic transducers of the ultrasonic probe 1, for example, by positive polar drive signals generated on the basis of the fed rate pulses to emits an ultrasonic pulse having the center frequency $f_0$ towards the subject.

A part of the ultrasonic pulse emitted in the subject is reflected at organ borders or tissues of the subject, having different sound impedances from each other. In this case, an ultrasonic reflected wave having, e.g., the center frequency $2f_0$ is newly generated from the ultrasonic reflected wave due to the non-linear characteristic of the subject tissues. In other words, the ultrasonic reflected wave reflected at the tissues of the subject and returning to the ultrasonic probe 1 is a mixture of the fundamental component having the center frequency $f_0$, the same as that in the transmission time, and the harmonic component having the center frequency $2f_0$.

The ultrasonic reflected wave reflected at the inside of the subject is received and converted into electrical receiving signals by the same ultrasonic probe 1 that used in the transmission time, amplified to a predetermined magnitude by the preamplifier 31 of the ultrasonic receiving unit 3, and converted into digital signals by the A/D converter 32. In addition, the digitalized receiving signals are provided with predetermined delay times by the beam former 33 on the basis of the control signals from the system control unit 12. The receiving signals are then subjected to an adding process with the adder 34 and the added receiving signal is fed to the signal processing unit 5.

On this occasion, delay times for focusing the ultrasonic reflective wave reflecting from the predetermined depth and other delay times for providing the ultrasonic reflected wave with strong receiving directivity in the scanning direction θ1 are set in the beam former 33 on the basis of the control signals from the system control unit 12.

Then, the selection circuit 51 of the signal processing unit 5 then selects the receiving signal fed from the adder 34 of the ultrasonic receiving unit 3, and the envelope detector 52 and the logarithmic converter 53 generate B mode data by applying envelope detection and logarithmic conversion to the receiving signal and store it in the memory circuit of the image data storage/processing unit 6.

When the generation of the B mode data in the scanning direction θ1 and its storage are completed according to the foregoing procedure, the transmission/reception direction of an ultrasonic wave is deflected to an angle: θp=θ1+(p−1)Δθ(p=2, - - - , P) by sequentially updating the angle by Δθ, and the ultrasonic wave is transmitted/received according to the same procedure as described above. On this occasion, the system control unit 12 generates the B mode data by sequentially updating the delay times of the transmission delay circuits 22 and the beam former 33 so as to correspond to the ultrasonic wave transmission/reception direction in accordance with the corresponding control signal.

The sector scanning is performed in the scanning direction from θ1 through θP with using an ultrasonic wave as described above. When the B mode data obtained for each scanning direction is sequentially stored in the image data storage/processing unit 6 and the B-mode image data is generated, the display image data generating circuit 91 of the image display unit 9 generates displaying image data by applying processes such as scanning conversion to the B-mode image data read out from the memory circuit of the image data storage/processing unit 6. Then, the conversion circuit 92 of the image display unit 9 displays the displaying image data on the monitor 93 of the image display unit 9 after applying D/A conversion and TV format conversion to it (step S4 in FIG. 3).

By sequentially performing ultrasonic wave transmission/reception in the scanning direction from θ1 through θP, the B-mode image data by transmission with low sound pressure is displayed on the monitor 93 of the image display unit 9 in real time, and, by monitoring the B-mode image data, the operator checks an operation of the apparatus, optimizes the imaging position relative to the subject, sets an apparatus gain and a dynamic range, and performs others.

Subsequently, when the foregoing monitoring is completed by observing the B-mode image data obtained by conducting the transmission with low sound pressure during the period τO, the operator inputs a generation-starting command of the THI image data with the aid of the input device 10 (step S5 in FIG. 3).

Upon reception of the command signal, the system control unit 12 performs the transmission with low sound pressure on the drive voltage $V_L$ and displays the B-mode image data on the monitor 93 of the image display unit 9 in real time in the same procedure as described above (step S6 in FIG. 3). When generation and display of the B-mode image data during the driving period $\tau_L$ of the transmission with low sound pressure are completed, in order to generate the THI image data, the sound output control unit 7 updates the drive voltage of the driving circuits 23 to the drive voltage $V_H$ for the transmission with high sound pressure.

Upon generation of the THI image data by conducting the transmission with high sound pressure, the transmission delay circuits 22 provide the rate pulses fed from the rate pulse generator 21 with delay times respectively for focusing an ultrasonic beam at a predetermined depth and for emitting it in the scanning direction θ1 and feed the rate pulses to the driving circuits 23.

Subsequently, the driving circuits 23 generate positive polar drive pulses in accordance with the timings of the rate pulses and drive the ultrasonic transducers of the ultrasonic probe 1 to emit the ultrasonic pulse having the center frequency $f_0$ towards the subject.

A part of the ultrasonic pulse emitted into the subject is reflected at the organ borders or the tissues of the subject, having different sound impedances from each other. In this case, in the same fashion as in the foregoing B-mode image data, the ultrasonic reflected wave has a harmonic component having an example center frequency of 2f0 newly generated therein due to the non-linear characteristic of the subject tissues. In addition, the harmonic component of the ultrasonic reflected wave obtained by conducting the transmission with high sound pressure is more significantly generated than that obtained by conducting the transmission with low sound pressure. It is known that the reason of generating this harmonic component is such that the transmitting speed of an ultrasonic pulse in the tissue of the subject depends on a sound pressure of the ultrasonic wave and that this property causes distortion of a receiving signal and thus generation of its harmonic component.

FIGS. 5 through 7 illustrate the foregoing harmonic component, wherein FIG. 5 shows a frequency spectrum of the ultrasonic pulse emitted into the subject and having the center frequency f0, and FIG. 6 shows a frequency spectrum of the ultrasonic reflected wave obtained from the inside of the subject. In other words, the frequency spectrum of the ultrasonic reflected wave has a fundamental component distributing with the center f0 and a harmonic component distributing with the center 2f0, and the harmonic component is smaller than the fundamental component generally by at least 20 dB.

In the ultrasonic diagnosis field, since an ultrasonic pulse having a broadband frequency spectrum is used in order to obtain an image with high resolution, the fundamental and harmonic components of its ultrasonic reflected wave likewise has a broadband spectrum, whereby a high frequency part of the fundamental component and a low frequency part of the harmonic component are not often separated from each other in frequency as shown in FIG. 6. As a method for extracting the harmonic component in such a case, the pulse inversion method is applied in the present embodiment.

The ultrasonic reflected wave reflected at the inside of the subject is converted into electrical receiving signals by the ultrasonic probe 1, converted into digital signals by the preamplifier 31 and the A/D converter 32, and the digital signals converted are subjected to phase-rectification and addition by the beam former 33 and the adder 34. On this occasion, delay times for focusing the ultrasonic reflective wave reflecting from the predetermined depth and other delay times for providing the ultrasonic reflected wave with strong receiving directivity in the scanning direction θ1 are set in the beam former 33. The phase-rectified and added receiving signal outputted from the adder 34 of the ultrasonic receiving unit 3 is temporally stored in the waveform memory 41 of the harmonic component extracting unit 4.

Then, the system control unit 12 transmits a control signal to the ultrasonic transmitting unit 2, switches each of the driving circuits 23 from a positive polar driving circuit so as to serve as a negative polar driving circuit, and transmits/receives an ultrasonic wave in the scanning direction θ1 by using a negative driving pulse. The receiving signal phase-rectified and added by the beam former 33 and the adder 34 of the ultrasonic receiving unit 3 is fed to the adder 42 with the aid of the waveform memory 41 of the waveform memory 4 and added to the receiving signal obtained from the positive polar driving signal previously stored in the waveform memory 41.

Figure 8:
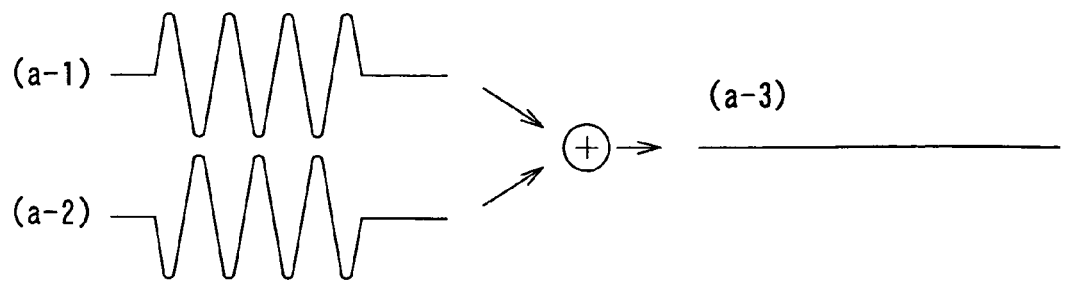
FIG. 8 is a figure showing the polarity of the fundamental component in the pulse inversion method according to the above-mentioned embodiment.
Figure 9:
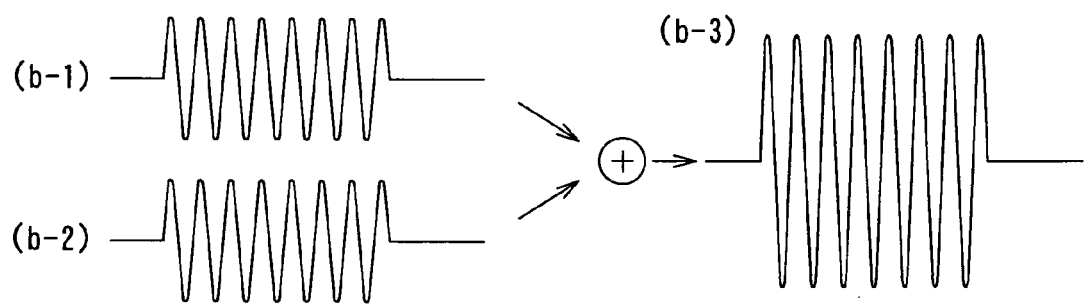
FIG. 9 is a figure showing the polarity of the harmonic component in the pulse inversion method according to the above-mentioned embodiment.

FIGS. 8 and 9 show polarities of fundamental and harmonic components of receiving signals and the results of adding the respective components with the pulse inversion method. Since the fundamental components of the receiving signals shown in FIG. 8, obtained in accordance with positive and negative polar driving signals respectively shown by (a-1) and (a-2), have mutually reverse polarities, the fundamental components can be canceled by adding them as shown by (a-3).

Whereas, since the harmonic components of receiving signals shown in FIG. 9, obtained in accordance with positive and negative polar driving signals respectively shown by (b-1) and (b-2), have the same polarity as each other, the amplitude of the harmonic component is made double by adding them as shown by (b-3).

With this, by adding the receiving signals obtained in accordance with positive and negative driving signals with the adder 42, the harmonic component is extracted as shown in FIG. 9 and is then transmitted to the filter circuit 43.

In the case where the fundamental component not removed by the pulse inversion method due to a motion of an organ, a body motion, or the like, is mixed in the foregoing harmonic component, the filter circuit 43 of the harmonic component extracting unit 4 removes this fundamental component and feeds only the harmonic component to the signal processing unit 5.

The selection circuit 51 of the signal processing unit 5 selects the foregoing harmonic component fed from the filter circuit 43. THI data is generated by applying envelope detection and logarithmic conversion to the selected harmonic component with the envelope detector 52 and the logarithmic converter 53 and then temporally stored in the image data storage/processing unit 6.

When generation of the THI data in the scanning direction θ1 and its storage are completed according to the foregoing procedure, the transmission/reception direction of an ultrasonic wave is deflected to an angle: θp=θ1+(p−1)Δθ(p=2, - - - , P) while sequentially updating the angle by Δθ, and the ultrasonic wave is transmitted/received according to the same procedure as described above. On this occasion, the system control unit 12 generates THI data while sequentially updating the delay times of the transmission delay circuits 22 and the beam former 33 so as to correspond to the ultrasonic wave transmission/reception direction in accordance with the corresponding control signals.

The sector scanning by using an ultrasonic wave is performed in the scanning direction θ1 through θP as described above. When the THI data obtained for each scanning direction is sequentially stored in the memory circuit of the image data storage/processing unit 6, and the THI image data is generated, the display image data generating circuit 91 of the image display unit 9 reads out the THI image data and displays it on the monitor 93 via the conversion circuit 92 after applying processes such as scanning conversion to it.

By sequentially performing ultrasonic wave transmission/reception in the scanning direction from θ1 through θP as described above, the THI image data obtained by conducting the transmission with high sound pressure is displayed on the monitor 93 of the image display unit 9 in real time. Hence, the operator diagnoses the subject with the aid of the THI image data and stores it in a storage device (not shown) if needed (step S7 in FIG. 3).

When the generation and the display of the THI image data as described above are conducted in the previously set driving period $\tau_H$, the process of the generation procedure moves to a so-called transmission with zero sound pressure in which no ultrasonic wave is transmitted/received (step S8 in FIG. 3). When a temperature ϕ of the ultrasonic probe 1 measured by the temperature measuring unit 11 during the driving period $\tau_H$ of the foregoing transmission with high sound pressure exceeds a prescribed temperature $\phi_{0X}$ (=$\phi_0$−Δϕ) taking into account a predetermined margin Δϕ with respect to the permissible temperature $\phi_0$ regulated by the heat generation regulation, generation of the THI image data by conducting the transmission with high sound pressure is finished on the basis of a signal for stopping the transmission with high sound pressure transmitted by the sound output control unit 7, and the process moves to the transmission with zero sound pressure (step S9 in FIG. 3).

Figure 10:
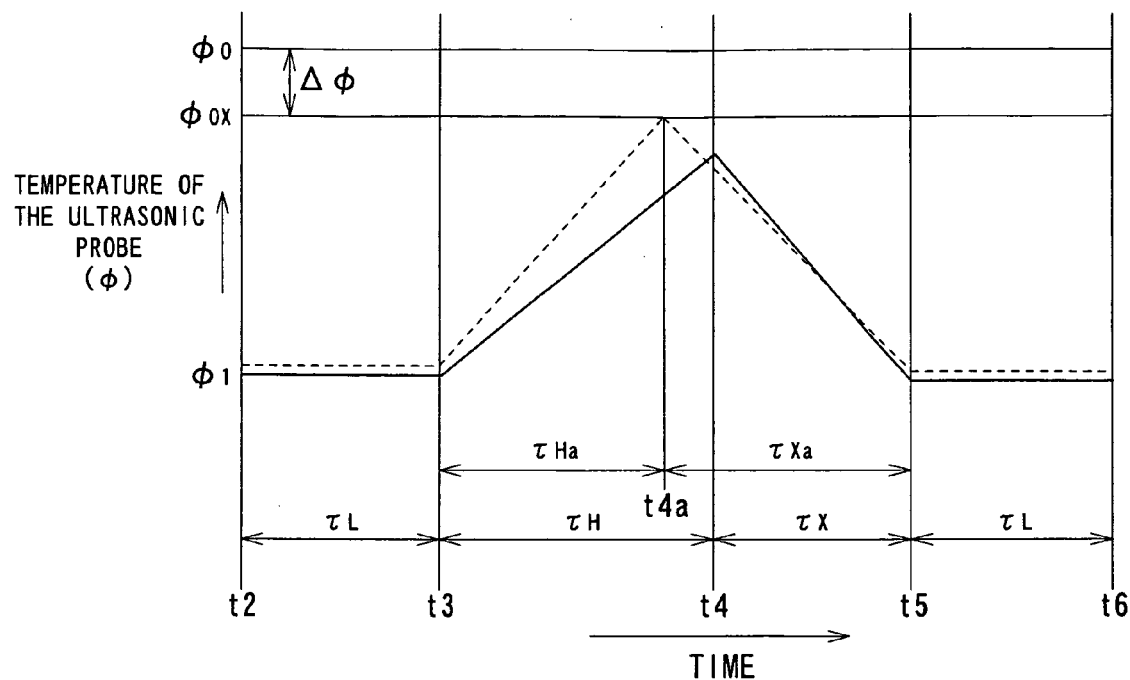
FIG. 10 a figure showing typically the temperature change of the ultrasonic probe measured by the temperature measuring unit according to the above-mentioned embodiment.

FIG. 10 shows two diagrammatic curves of temperatures of the ultrasonic probe 1 measured by the temperature measuring unit 11, caused by the transmissions with low, high, and zero sound pressure, for example, during the period from times t2 through t6 shown in FIG. 2, illustrating that the temperature ϕ of the ultrasonic probe 1 rises, falls, and is kept invariable due to the transmissions with high, low, and zero sound pressure, respectively.

In other words, according to the temperature curves of the ultrasonic probe 1 shown in FIG. 10, the temperature of the ultrasonic probe 1 is maintained at a predetermined initial temperature $\phi_1$ at the time of the transmission with low sound pressure from times t2 to t3 and rises gradually due to the transmission with high sound pressure starting from a time t3. On this occasion, when the probe temperature ϕ does not reach the prescribed temperature $\phi_{0X}$ before a time t4 initially set as shown by a solid line indicating the temperature curve, the transmission with high sound pressure is finished at the time t4, and the process moves to the transmission with zero sound pressure.

When the probe temperature ϕ reaches the prescribed temperature $\phi_{0X}$ at a time t4a before the time t4 initially set (i.e., t4a<t4) as shown by a dashed line indicating the temperature curve, the transmission with high sound pressure is finished at the time t4a, and the transmission with zero sound pressure starts.

More particularly, on the basis of the drive voltages $V_L$ and $V_H$ and the driving periods $\tau_L$ and $\tau_H$, set by the operator, of the respective transmissions with low and high sound pressure and the permissible transmission sound output per unit time regulated by the sound output regulation, the sound output control unit 7 calculates the period $\tau_X$ of the transmission with zero sound pressure and updates the driving period $\tau_H$ of the transmission with high sound pressure by comparing the temperature ϕ of the ultrasonic probe 1 with the prescribed temperature $\phi_{0X}$ based on the heat regulation.

When the probe temperature ϕ reaches the prescribed temperature $\phi_{0X}$ at the time t4a as described above, while the transmission with zero sound pressure can be finished at a time t5 lapsed by a period $\tau_{Xa}$ from the time t4a as shown in FIG. 10, it may be finished at a time lapsed by a period $\tau_X$ from the time t4a.

When generation and display of the THI image data are completed and the transmission with zero sound pressure starts according to the foregoing procedure (step S10 in FIG. 3), the lapsed time measuring circuit (not shown) of the sound output control unit 7 measures a lapsed period $\tau_Y$ of the transmission with zero sound pressure and calculates a command-input waiting time $\tau_Z$ for the generation start of the THI image data by calculating a difference between the lapsed period $\tau_Y$ and the period $\tau_X$ or $\tau_{Xa}$ of the transmission with zero sound pressure previously calculated or updated by the sound output parameter operation unit 8. Information about the command-input waiting time $\tau_Z$ is fed to the image display unit 9 with the aid of the system control unit 12 and displayed on the monitor 93 (step S11 in FIG. 3).

Figure 11:
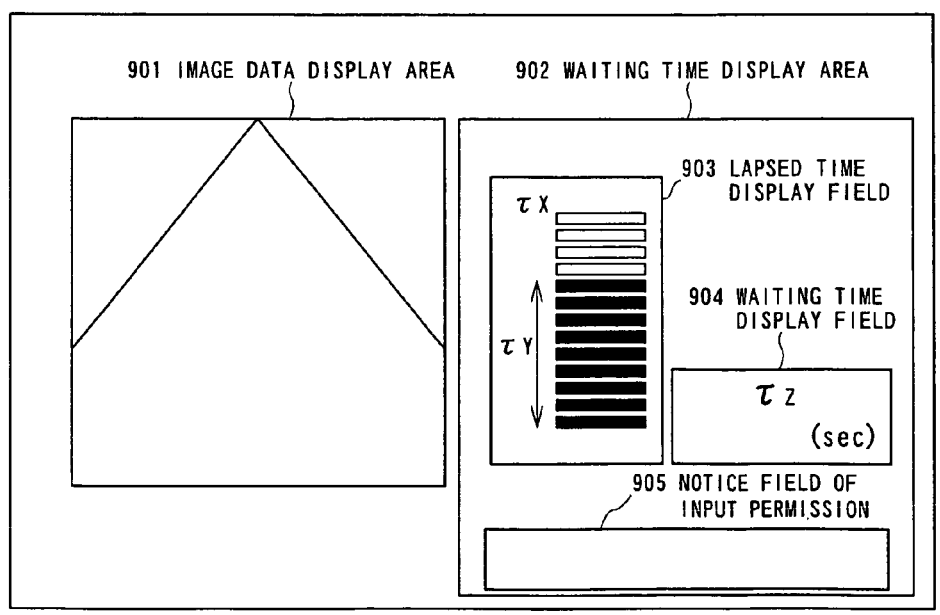
FIG. 11 is a figure showing the example of a display of command input waiting time.

FIG. 11 shows example display of a command-input waiting time. In the figure, the monitor 93 of the image display unit 9 has an image data display area 901 and a waiting time display area 902 set therein, respectively, for displaying image data and command-input waiting time information. The waiting time display area 902 has a lapsed time display field 903, a waiting time display field 904, and a notice field of input permission 905 set therein.

Thus, the lapsed period $\tau_Y$ of the transmission with zero sound pressure, with respect to the period $\tau_X$ (or $\tau_{Xa}$) of the transmission with zero sound pressure, is displayed in the lapsed time display field 903, and the command-input waiting time $\tau_Z$ (=$\tau_X$ (or $\tau_{Xa}$)−$\tau_Y$) for the THI image data obtained as a difference between the period $\tau_X$ (or $\tau_{Xa}$) of the transmission with zero sound pressure and the lapsed period $\tau_Y$ is displayed in the waiting time display field 904. In addition, when the command-input waiting time $\tau_Z$ is not greater than zero second (step S12 in FIG. 3), input permission information indicating permission of a command input for generation start of the THI image data is displayed in the notice field of input permission 905 (step S13 in FIG. 3).

The observer having monitored the input permission information inputs again a generation-starting command of the THI image data with the aid of the input device 10 (step S5 in FIG. 3). The system control unit 12 having received the command signal carries out the transmission with low sound pressure on the drive voltage $V_L$ during the driving period $\tau_L$ in accordance with the same procedure as described above by controlling the sound output control unit 7 and displays the obtained B-mode image data for use in monitoring, with the aid of the image display unit 9 in real time (step S6 in FIG. 3).

Subsequently, in order to generate the THI image data, the sound output control unit 7 updates the drive voltage of the driving circuits 23 to the drive voltage $V_H$ for the transmission with high sound pressure to generate and store the THI image data during the driving period $\tau_H$ or the driving period $\tau_{Ha}$ after which the signal for stopping the transmission with high sound pressure is to be transmitted (steps S7 to S9 in FIG. 3), and then the transmission with zero sound pressure is conducted during the driving period $\tau_X$ (or $\tau_{Xa}$) (steps S10 to S12 in FIG. 3).

As described above, with the repetitive operation from step 5 through step 13, generation and display of the B-mode image data intended for monitoring, obtained by conducting the transmission with low sound pressure, generation and display of the highly sensitive THI image data obtained by conducting the transmission with high sound pressure, and the transmission with zero sound pressure for reducing heat generation and a sound output of the ultrasonic probe 1 are repeated.

According to the above described embodiment, by repeating generation of the THI image data by conducting the transmission with high sound pressure and the transmission with zero sound pressure, the highly sensitive THI image data can be obtained without exceeding the permissible transmission sound output regulated by the sound output regulation.

In addition, since generation and display of the B-mode image data by the transmission with low sound pressure during the period $\tau_L$ are conducted prior to each generation of the THI image data during the period τH, an imaging position and an operation of the apparatus can be checked in advance, thereby always generating the THI image data under suitable conditions.

Also, since the period of the transmission with zero sound pressure is calculated on the basis of the previously set drive voltages and driving periods of the respective transmissions with high and low sound pressure and the foregoing permissible transmission sound output, the transmission sound outputs of the respective transmissions with low and high sound pressure can be easily controlled.

Further, since the foregoing ultrasonic diagnostic apparatus has a function of measuring the temperature of the ultrasonic probe and updating the driving period of the transmission with high sound pressure on the basis of the measured temperature, the highly sensitive and high resolution THI image data can be generated while complying with not only the sound output regulation but also the heat regulation of the ultrasonic probe, thereby improving the diagnosis efficiency of the apparatus.

According to the present embodiment, since an input waiting time for a generation-starting command of the THI image data calculated on the basis of the lapsed time of the transmission with zero sound pressure and the foregoing driving period is displayed on the display unit, the operator can easily and accurately grasp an input timing of the generation-starting command and hence obtain the high resolution THI image data at a desired timing, thereby drastically improving diagnosis efficiency.

While the preferred embodiment of the present invention has been described, the present invention is not limited to the foregoing embodiment and a variety of modifications are possible. For example, while the transmission with low sound pressure during the period $\tau_L$ are set prior to the corresponding transmissions with high sound pressure according to the foregoing embodiment, the transmission with low sound pressure is not always needed. For example, as long as sufficient monitoring can be conducted on the transmission with low sound pressure from times t1 to t2 shown in FIG. 2, the transmission with low sound pressure during the period $\tau_L$ prior to the corresponding transmission with high sound pressure can be eliminated. In this case, it is preferable that the period $\tau_X$ of the transmission with zero sound pressure be calculated on the basis of the previously set drive voltage $V_H$ and driving period $\tau_H$ of the transmission with high sound pressure and the permissible transmission sound output $W_0$, and the driving period $\tau_H$ be then updated on the basis of the temperature information of the ultrasonic probe 1 obtained with the aid of the temperature measuring unit 11.

Alternatively, the foregoing transmission with zero sound pressure can be replaced with the transmission with low sound pressure. More particularly, the period $\tau_L$ of the transmission with low sound pressure may be calculated on the basis of the previously set drive voltage $V_H$ and driving period $\tau_H$ of the transmission with high sound pressure and the permissible transmission sound output $W_0$, and the driving period $\tau_H$ may be then updated on the basis of the temperature information of the ultrasonic probe 1 obtained with the aid of the temperature measuring unit 11.

According to the foregoing embodiment, the drive voltages and the driving periods of the respective transmissions with high and low sound pressure, and the period of transmission with zero sound pressure are first set on the basis of the sound output regulation, and the driving period of the transmission with high sound pressure is then updated on the basis of the measured temperature of the ultrasonic probe 1. However, when compliance of heat generation of the ultrasonic probe 1 with the heat regulation is especially important, the periods of the respective transmissions with high sound pressure and the transmission with zero sound pressure or the periods of the respective transmissions with low, high, and zero sound pressure may be set on the basis of the measured temperature of the ultrasonic probe 1.

While the information about the command-input waiting time for the THI image data is displayed on the monitor 93 of the image display unit 9 according to the foregoing embodiment, it may be displayed on a display panel of the input device 10. A command input permission also may be noticed by blinking of a light-emitting diode (LED) or the like or with the aid of an audio system included, for example, in the input device 10.

While the transmission with high sound pressure according to the foregoing embodiment is intended for generating the THI image data by using the second harmonic component, it may be intended for generating the THI image data by using a nonlinear component, such as a harmonics component of three times or more or a 1.5 time component. While the ultrasonic probe 1 according to the foregoing embodiment has ultrasonic transducers arranged in one dimension, it may have the transducers arranged in two dimensions.

What is claimed is:

1. An ultrasonic diagnostic apparatus, comprising:
   a driving circuit configured to drive an ultrasonic transducer to transmit an ultrasonic wave to a subject, wherein the driving circuit is configured to transmit (a) a first ultrasonic transmission with a first period during which the ultrasonic wave has a first sound output, and (b) a second ultrasonic transmission with a second period during which the ultrasonic wave has a second sound output lower than the first sound output, and configured to stop ultrasonic transmission during a non-driving period between the first period and the second period;
   a receiving circuit configured to generate a reception signal from received ultrasonic waves;
   a nonlinear component extracting circuit configured to extract a nonlinear component from the reception signal corresponding to the first ultrasonic transmission; and
   processing circuitry configured to generate first image data based on the nonlinear component;
   generate second image data from a reception signal corresponding to the second ultrasonic transmission;
   calculate the non-driving period using at least the first sound output and the first period; and
   control the drive circuit to perform the first ultrasonic transmission during the first period, stop the ultrasonic transmission during the calculated non-driving period between the first period and the second period, and perform the second ultrasonic transmission during the second period after the calculated non-driving period.

2. The ultrasonic diagnostic apparatus according to claim 1, wherein the processing circuitry is further configured to inform whether it is possible to perform the first ultrasonic transmission.

3. The ultrasonic diagnostic apparatus according to claim 1, wherein the processing circuitry controls the driving circuit to turn off and stop the first ultrasonic transmission during the calculated non-driving period, after the first ultrasonic transmission with the higher sound pressure is continuously performed during the first period.

4. The ultrasonic diagnostic apparatus according to claim 3, further comprising an input interface configured to input an instruction signal for starting the first ultrasonic transmission with the higher sound pressure,
   wherein the processing circuitry controls the driving circuit to start the first ultrasonic transmission with the higher sound pressure when the instruction signal is inputted to the input interface after a lapse of the calculated non-driving period.

5. The ultrasonic diagnostic apparatus according to claim 3, further comprising a display configured to display a lapse of the calculated non-driving period.

6. The ultrasonic diagnostic apparatus according to claim 5, wherein the display displays the lapse using at least one of a character and a typical figure indicating at least one of a remaining time until the calculated non-driving period expires and a lapsed time after the first ultrasonic transmission.

7. The ultrasonic diagnostic apparatus according to claim 1, further comprising a temperature measurement circuit configured to measure a temperature of an ultrasonic probe having the ultrasonic transducer,
   wherein the processing circuitry turns off, even during the first period, the first ultrasonic transmission when a temperature measurement value measured by the temperature measurement circuit exceeds a specified temperature value set up previously.

8. The ultrasonic diagnostic apparatus according to claim 7, wherein the processing circuitry sets up the specified temperature value based on an allowable temperature of a heat regulation, the allowable temperature being set up in consideration of safety to the subject.

9. An image data generating method, comprising:
   driving an ultrasonic transducer to transmit an ultrasonic wave to a subject, wherein the driving step including transmitting (a) a first ultrasonic transmission with a first period during which the ultrasonic wave has a first sound output, and (b) a second ultrasonic transmission with a second period during which the ultrasonic wave has a second sound output lower than the first sound output, and stopping ultrasonic transmission during a non-driving period between the first period and the second period;
   generating a reception signal from received ultrasonic waves;
   extracting a nonlinear component from the reception signal corresponding to the first ultrasonic transmission;
   generating first image data based on the nonlinear component;
   generating second image data from a reception signal corresponding to the second ultrasonic transmission;
   calculating the non-driving period using at least the first sound output and the first period; and
   controlling the driving of the ultrasonic transducer to perform the first ultrasonic transmission during the first period, stop the ultrasonic transmission during the calculated non-driving period between the first period and the second period, and perform the second ultrasonic transmission during the second period after the calculated non-driving period.

10. An image data generating method according to claim 9, further comprising a step of informing whether it is possible to perform the first ultrasonic transmission.

11. An image data generating method according to claim 9, wherein the ultrasonic transducer is driven to stop the first ultrasonic transmission during the calculated non-driving period, after the first ultrasonic transmission with the higher sound pressure is continuously performed during the first period.

12. An image data generating method according to claim 11, further comprising a step of inputting an instruction signal for starting the first ultrasonic transmission with the higher sound pressure,
   wherein the first ultrasonic transmission with the higher sound pressure starts when the instruction signal is inputted after a lapse of the calculated non-driving period.

13. An image data generating method according to claim 11, further comprising a step of informing a lapse of the calculated non-driving period.

14. An image data generating method according to claim 13, wherein the lapse is informed using at least one of a character and a typical figure indicating at least one of a remaining time until the calculated non-driving period expires and a lapsed time after the first ultrasonic transmission.

15. An image data generating method according to claim 9, further comprising a step of measuring a temperature of an ultrasonic probe having the ultrasonic transducer,
> wherein the first ultrasonic transmission is turned off, even during the first period, when the measured temperature exceeds a specified temperature value set up previously.

16. An image data generating method according to claim 15, wherein the specified temperature value is set up based on an allowable temperature of a heat regulation, the allowable temperature being set up in consideration of safety to the subject.

* * * * *